United States Patent
Giuliani et al.

(10) Patent No.: US 9,539,191 B2
(45) Date of Patent: *Jan. 10, 2017

(54) COMPOSITION FOR COSMETIC USE SUITABLE TO PRODUCE A PIGMENTATION EFFECT ON HAIR

(71) Applicant: Giuliani S.P.A., Milan (IT)

(72) Inventors: Giammaria Giuliani, Milan (IT); Ralf Paus, Hamburg (DE); Anna Benedusi, Milan (IT); Barbara Marzani, Carbonara al Ticino (IT); Sergio Baroni, Villa D'Adda (IT)

(73) Assignee: GIULIANI S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/764,914

(22) PCT Filed: Feb. 17, 2014

(86) PCT No.: PCT/IB2014/059048
§ 371 (c)(1),
(2) Date: Jul. 30, 2015

(87) PCT Pub. No.: WO2014/125452
PCT Pub. Date: Aug. 21, 2014

(65) Prior Publication Data
US 2015/0366770 A1    Dec. 24, 2015

(30) Foreign Application Priority Data
Feb. 18, 2013   (IT) .............................. MI2013A0218

(51) Int. Cl.
A61K 8/41   (2006.01)
A61K 8/69   (2006.01)
(Continued)

(52) U.S. Cl.
CPC ................. *A61K 8/41* (2013.01); *A61K 8/411* (2013.01); *A61K 8/69* (2013.01); *A61Q 5/00* (2013.01);
(Continued)

(58) Field of Classification Search
None
See application file for complete search history.

(56) References Cited

U.S. PATENT DOCUMENTS

| 7,699,897 B2 | 4/2010 | Nguyen et al. |
| 9,241,888 B2* | 1/2016 | Giuliani ................... A61K 8/41 |
| 2009/0070945 A1 | 3/2009 | Nguyen et al. |

FOREIGN PATENT DOCUMENTS

| WO | 9937277 A1 | 7/1999 |
| WO | 03063851 A1 | 8/2003 |
| WO | 2011013087 A1 | 3/2011 |

OTHER PUBLICATIONS

Notification of Transmittal of the International Preliminary Report on Patentability dated Sep. 7, 2015 for International Application No. PCT/IB2014/059048.
(Continued)

*Primary Examiner* — Bethany Barham
*Assistant Examiner* — Barbara Frazier
(74) *Attorney, Agent, or Firm* — Abelman, Frayne & Schwab

(57) ABSTRACT

The invention concerns the use of compounds with formula (I) R—N1-spermidine, or 1,4-butandiamin,N-(3-amino propyl)-N1-R, (I) $H_2N-(CH_2)_3-N^1(R)-(CH_2)_4-NH_2$ either as such or in the form of a pharmaceutically acceptable derivative, such as an active ingredient in a cosmetic composition designed to promote hair pigmentation, particularly the pigmentation of the shaft, and a composition suitable to achieve said pigmentation effect and containing
(Continued)

said active ingredient, either as such or in the form of a pharmaceutically acceptable derivative such as a salt, for topical administration.

5 Claims, 3 Drawing Sheets

(51) Int. Cl.
*A61Q 5/00* (2006.01)
*A61Q 5/10* (2006.01)
(52) U.S. Cl.
CPC ............. *A61Q 5/10* (2013.01); *A61K 2800/42* (2013.01); *A61K 2800/78* (2013.01)

(56) References Cited

OTHER PUBLICATIONS

International Search Report for PCT/IB2014/059048 dated Apr. 25, 2014.

\* cited by examiner

Control (vehicle)

Methyl-spermidine 0.5 µM

Methyl-spermidine 1.5 µM

COMPOSITION FOR COSMETIC USE SUITABLE TO PRODUCE A PIGMENTATION EFFECT ON HAIR

CROSS-REFERENCE TO RELATED APPLICATIONS

This application is a National Phase of PCT/IB2014/059048, filed 17 Feb. 2014, which claims priority from Italian Application No. MI 2013A000218 filed 18 Feb. 2013, the disclosures of which are incorporated herein by reference.

FIELD OF THE INVENTION

This invention concerns a pigmentation effect on human hair, and the use of active ingredients to achieve said purpose.

STATE OF THE ART

The human hair follicle is a complex organ in which interactions between epithelial cells (e.g. different lines of keratinocytes, endothelium), mesenchymal cells (e.g. fibroblasts of the dermal papilla, fibroblasts of the connective tissue sheath), neuroectodermal cells (nerves, melanocytes) and transiting migrating cells (immune cells, mastocytes) take place.

The growth and pigmentation of hair fibres are influenced by several intrinsic factors, including changes that depend on the hair cycle, body distribution, differences in race and genre, variable hormone sensitivity, genetic defects and age-related changes. The growth of hair is also influenced by environmental variables, including climate and seasons, polluting substances, toxins and exposure to chemical substances. The differences observed between regulation of pigmentation in the epidermis and in hair follicles basically mirror the compartments of the pigmentation system of mammal skin.

Melanocytes present in the epidermis, in the bulb of the hair follicle and in the external root sheath of the hair follicle are mutually different. The major differences lie in the respective melanocyte-keratinocyte functional units. The melanin unit of the hair bulb is found in the bulb in the proximal anagen, which is an immunologically distinct region of the skin. Said unit comprises one melanocyte every 5 keratinocytes in the hair bulb, and one melanocyte every keratinocyte in the basal layer of the hair bulb matrix. Conversely, each epidermal melanocyte is associated with 36 vital keratinocytes in the immunocompetent epidermal melanin unit.

The most evident difference between these two melanocyte populations is that the activity of the melanocyte in the hair bulb is subjected to cycle control and, therefore, the corresponding melanogenesis is strictly associated with the growth cycle of hair and is, hence, discontinuous. Epidermal melanogenesis, instead, appears to be continuous.

In fact, the hair cycle includes periods of melanocyte proliferation (during the early anagen phase), maturation (from half way through to the end of the anagen phase), and death of melanocytes by apoptosis (during the early catagen phase).

Every hair cycle is associated with the reconstruction of a pigment unit that is intact at least for the first ten cycles (Tobin, Int. J. Cosmetic Science, 2008; Tobin and Paus, Exp. Gerontol., 2001). Biosynthesis of melanin and its subsequent transfer from melanocytes to keratinocytes in the hair bulb depend on the availability of melanin precursors and on complex signal transduction mechanisms.

Though follicular and epidermal melanocytes have common traits, follicular melanocytes seem to be more sensitive than epidermal ones to the aging process. The pigmentary unit of hair plays an important role as environmental sensor, and also an important physiological function. In practice, pigments contribute to the rapid excretion of heavy metals and toxins from the body through their selective bond with melanin (Tobin, Int. J. Cosmetic Science, 2008).

When grey and white hair appear, they suggest age-related and genetically regulated exhaustion of the pigment-forming potential of each hair follicle. The aging of melanocytes can be associated with damage mediated by reactive oxygen species to the nucleus and to mitochondrial DNA with subsequent build up of mutations with age, besides an evident alteration in antioxidant mechanisms or in pro-apoptotic and anti-apoptotic factors in cells. Oxidative stress is generated by several factors, such as environmental factors and endogenous changes (radiations, inflammation, emotional stress) that accelerate the aging process.

Other data in the literature report that the continuous synthesis of melanin during the growth phases of hair (anagen) generates high levels of oxidative stress, and that melanocytes are particularly sensitive to aging induced by free radicals.

In fact, it has been proven that the pigmentary unit of grey hair contains apoptotic melanocytes and also presents a high level of oxidative stress. (Arck et al., FASEB Journal, 2006)

Patent application WO2011/013087 in the name of the Applicant describes compositions with pigmentation activities of hair based on spermidine. However, in the case of formulations for topical use, spermidine, like other polyamines, is subjected to oxidation because, during topical application on the scalp, it remains in contact with the air for a certain period of time before being absorbed by the skin to perform its action. The possible oxidation of spermidine during said period prior to absorption would produce oxidation products that are not active anymore.

Moreover, the scope of this invention is to improve the pigmentation action of hair.

DESCRIPTION OF THE INVENTION

It has now been surprisingly found, and this is the object of the invention, that said technical problem can be solved by using a compound with general formula (I): R—$N^1$-spermidine as defined below, either as such or as a pharmaceutically acceptable derivative such as a salt.

The invention relates to the use of compounds with formula (I) R—$N^1$-spermidine, or 1,4-butandiamin,N-(3-amino propyl)-$N^1$—R,

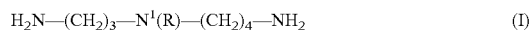

$$H_2N\text{—}(CH_2)_3\text{—}N^1(R)\text{—}(CH_2)_4\text{—}NH_2 \qquad (I)$$

wherein R is a substituent that is bound to the secondary amine group of spermidine, chosen from saturated or unsaturated, linear or branched alkyl groups formed by 1 to 6 atoms of carbon, in which one or more carbon atoms are optionally replaced by fluorine, namely methyl, ethyl, trifluoromethyl, trifluoroethyl, propyl, isopropyl, butyl, isobutyl, pentyl, hexyl, ethylene, vinyl, propylene, butylene; aryl or aryl-alkyl groups, such as phenyl, naphthyl, benzyl, tolyl, in which one or more carbon atoms are optionally replaced by fluorine, and wherein said aryl-alkyl groups include saturated or unsaturated, linear or branched alkyl groups formed by 1 to 6 atoms of carbon, in which one or more carbon atoms are optionally replaced by fluorine, namely methyl, ethyl, trifluoromethyl, trifluoroethyl, propyl, isopropyl, butyl, isobutyl, pentyl, hexyl, ethylene, vinyl, propylene, butylene;

saturated or unsaturated cycloalkyl groups formed by 3 to 8 atoms of carbon that are optionally replaced by saturated or unsaturated, linear or branched alkyl groups formed by 1 to 6 atoms of carbon, in which one or more carbon atoms are optionally replaced by fluorine, namely methyl, ethyl, trifluoromethyl, trifluoroethyl, propyl, isopropyl, butyl, isobutyl, pentyl, hexyl, ethylene, vinyl, propylene, butylene; or their pharmaceutically acceptable salt, to produce a melanogenetic action in hair and to promote its pigmentation, particularly pigmentation of the shaft.

The compounds of the general formula (I) are active within the scope of this invention, and stable in air to allow effective application for topical use on the scalp without being transformed into a different inactive substance as a result of oxidation.

These compounds of the general formula (I) have a considerable melanogenetic action on hair and can, therefore, be effectively used for topical application on the scalp to promote hair pigmentation, particularly pigmentation of the shaft.

In this invention, said action defines the use of a compound with formula (I) in humans as a natural pigmentation agent that is void of negative side effects that are, for instance, typical of hair dyes.

The object of this invention is also a composition for cosmetic use designed to perform said pigmentation effect; hence, it contains as active ingredient at least one compound with formula (I), either as such or in the form of a pharmaceutically acceptable derivative, such as a salt, for topical administration.

Suitable forms for topical use include, for example, a lotion, a conditioner, a shampoo, a mask or a gel.

If said compound with formula (I) is in the form of a pharmaceutically acceptable derivative, such as a salt, it is preferably a maleic acid salt, such as trimaleate, or a hydrochloric acid salt, such as trichlorohydrate.

Every other salt of an organic or inorganic acid that is pharmaceutically acceptable for a formulation for topical use is suitable.

A preferred compound with formula (I) for this invention is $N^1$-methyl-spermidine, or N-(3-amino propyl)-$N^1$-methyl-1,4-butandiammine (CAS Registry Number 51460-23-2), with formula:

$$H_2N-(CH_2)_3-N^1(CH_3)-(CH_2)_4-NH_2 \quad (II)$$

used in a composition of the invention either as such or as a pharmaceutically acceptable salt such as, for instance, trimaleate or trichlorohydrate (3HCl).

Another preferred compound with formula (I) for this invention is $N^1$-cyclohexyl-spermidine, or N-(3-amino propyl)-$N^1$-cyclohexyl-1,4-butandiammine (CAS Registry Number 183070-28-2), with formula:

$$H_2N-(CH_2)_3-N^1(C_6H_{11})-(CH_2)_4-NH_2 \quad (III)$$

used in a composition of the invention either as such or as a pharmaceutically acceptable salt such as, for instance, trimaleate or trichlorohydrate (3HCl).

Another preferred compound with general formula (I) for this invention is $N^1$-ethyl-spermidine, or N-(3-amino propyl)-$N^1$-ethyl-1,4-butandiammine with formula:

$$H_2N-(CH_2)_3-N^1(C_2H_5)-(CH_2)_4-NH_2 \quad (IV)$$

either as such or the pharmaceutically acceptable salt.

Another preferred compound with general formula (I) for this invention is $N^1$-propyl-spermidine, or N-(3-amino propyl)-$N^1$-propyl-1,4-butandiammine with formula:

$$H_2N-(CH_2)_3-N^1(C_3H_7)-(CH_2)_4-NH_2 \quad (V)$$

either as such or the pharmaceutically acceptable salt.

A compound with formula (I), either as such or in the form of a pharmaceutically acceptable derivative, such as a salt, is contained in a composition of the invention in a quantity that is preferably within the following weight/volume concentration ranges of the solution:

from 0.01 to 0.30 g/100 mL
from 0.001 to 0.30 g/100 mL
from 0.00010 to 0.15 g/100 mL
from 0.005 to 0.30 g/100 mL
from 0.05 to 0.210 g/100 mL Some examples of compositions formulated based on the invention for topical use on the scalp are described below but not as a limitation.

The quantities of components are expressed in weight per volume percentage, consistently with the concentration ranges indicated.

Example 1

| HAIR GEL | |
| --- | --- |
| Component (INCI name) | Quantity w/v (%) |
| Polyacrylate-14 | 0.05-1.00 |
| PEG-40 Hydrogenated castor oil | 0.20-3.00 |
| Parfum | 0.10-1.00 |
| Sodium Hydroxymethylglycinate | 0.04-0.49 |
| Panthenol | 0.10-0.50 |
| Sorbitol | 0.10-1.00 |
| N1-methyl, N1-(3-amino propyl)-1,4-Butanediamine | 0.010-0.30 |
| Disodium EDTA | 0.025-0.10 |
| Hydroxypropyl guar | 0.20-1.00 |
| Benzophenone-4 | 0.20-0.25 |
| Polyquaternium-11 | 0.05-0.50 |
| Aqua | qs to 100 mL |

Example 2

| HAIR CONDITIONER | |
| --- | --- |
| Component (INCI name) | Quantity w/v (%) |
| Disodium EDTA | 0.025-0.05 |
| Xylitol | 0.50-1.50 |
| Panthenol | 0.50-1.50 |
| Sericin | 0.050-0.20 |
| Hydroxyethyl cellulose | 0.10-0.90 |
| Cetrimonium chloride | 0.50-5.00 |
| Bis-Isobutyl PEG/PPG-20/35/ Amodimethicone Copolymer | 0.05-0.75 |
| Cetyl Ethylhexanoate | 0.05-0.40 |
| Polysorbate 80 | 0.05-0.40 |
| Butylene Glycol | 0.05-3.00 |
| Cyclopentasiloxane | 0.10-3.00 |
| C12-13 alkyl lactate | 0.50-5.00 |
| Glyceryl stearate | 1.00-6.00 |
| PEG-100 stearate | 0.50-4.00 |
| Dimethicone | 1.00-6.00 |
| Dimethiconol | 0.10-1.00 |
| Cetearyl alcohol | 1.00-7.00 |
| Phytantriol | 0.050-1.00 |
| Phenoxyethanol | 0.30-0.90 |

HAIR CONDITIONER

| Component (INCI name) | Quantity w/v (%) |
| --- | --- |
| Methylparaben | 0.020-0.20 |
| Ethylparaben | 0.020-0.20 |
| Zeaxanthin | 0.00005-0.00030 |
| Rutin | 0.0005-0.003 |
| N1-methyl, N1-(3-amino propyl)-1,4-Butanediamine | 0.00010-0.15 |
| Parfum | 0.10-0.30 |
| Aqua | qs to 100 mL |

Example 3

AFTER-SHAMPOO WATER

| Component (INCI name) | Quantity w/v (%) |
| --- | --- |
| Sodium benzoate | 0.04-0.10 |
| Potassium sorbate | 0.04-0.10 |
| Panthenol | 0.10-0.50 |
| N1-methyl, N1-(3-aminopropyl)-1,4-Butanediamine | 0.010-0.30 |
| Disodium EDTA | 0.025-0.05 |
| Parfum | 0.10-0.20 |
| PPG-26 Buteth-26 | 0.20-0.50 |
| Peg-40 Hydrogenated castor oil | 0.20-0.50 |
| Lactic acid | qs to pH 5.0 |
| Aqua | qs to 100 mL |

Example 4

ANDROGENETIC ALOPECIA TREATMENT LOTION

| Component (INCI name) | Quantity w/v (%) |
| --- | --- |
| Hydroxypropyltrimonium Hyaluronate | 0.005-0.50 |
| Polyurethane-26 | 0.004-4.0 |
| Lecithin (Glycine max L.) | 0.005-5.0 |
| Alcohol denat. | 15.0-20.0 |
| N1-methyl, N1-(3-aminopropyl)-1,4-Butanediamine | 0.005-0.30 |
| Biotin | 0.01-0.10 |
| Calcium pantothenate | 0.1-3.0 |
| Rutin | 0.001-0.05 |
| PEG-40 Hydrogenated Castor Oil | 0.5-2.0 |
| Octadecyl Di-t-butyl-4-hydroxyhydrocinnamate | 0.05 |
| Parfum | 0.20 |
| Zeaxanthin | 0.002-0.01 |
| Helianthus annuus seed oil | 0.001-0.01 |
| Lactic acid | qs to pH 5.0 |
| Aqua | qs to 100 mL |

Example 5

ANDROGENETIC ALOPECIA TREATMENT SHAMPOO

| Component (INCI name) | Quantity w/v (%) |
| --- | --- |
| Disodium Laureth Sulfosuccinate | 1.00-5.00 |
| Magnesium Laureth Sulfate | 5.00-9.00 |
| PEG-7 Glyceryl Cocoate | 0.50-1.00 |
| Cocamide MIPA | 0.50-2.00 |
| Peg-200 Hydrogenated Glyceryl Palmate | 0.50-2.00 |
| Polyquaternium-10 | 0.10-0.50 |
| Sodium Lauroyl Sarcosinate | 1.00-4.00 |
| Tetrasodium EDTA | 0.05-0.20 |
| N1-methyl, N1-(3-aminopropyl)-1,4-Butanediamine | 0.001-0.30 |
| Biotin | 0.01-0.10 |
| Calcium pantothenate | 0.01-3.0 |
| Potassium Undecilenoyl Wheat Protein | 0.50-1.00 |
| Laureth-4 | 0.01-0.80 |
| Parfum | 0.10-0.80 |
| Glycol Distearate | 0.50-1.00 |
| Laureth-7 | 0.50-0.80 |
| Sodium Cocoamphoacetate | 0.05-3.00 |
| Cocamidopropyl Betaine | 0.01-2.00 |
| Sodium Laureth Sulfate | 0.01-3.00 |
| Sodium Hydroxymethylglycinate | 0.20-0.45 |
| Sodium hydroxyde | qs |
| Citric acid | qs |
| Aqua | qs to 100 mL |

Example 6

INTENSIVE HAIR CARE SERUM

| Component (INCI name) | Quantity w/v (%) |
| --- | --- |
| Alcohol denat. Type C | 10.00-20.00 |
| Calcium pantothenate | 0.05-2.00 |
| N1-methyl, N1-(3-aminopropyl)-1,4-Butanediamine | 0.05-0.210 |
| Potassium octatrienoate | 0.001-0.18 |
| Biotin | 0.005-0.020 |
| Ajuga reptans leaf extract | 0.001-0.10 |
| *Lactobacillus* soy ferment | 0.01-0.15 |
| Panthenol | 0.10-1.00 |
| Hydroxypropyltrimonium Hyaluronate | 0.002-0.50 |
| Polyurethane-26 | 0.004-4.0 |
| Lecithin (Glycine max L.) | 0.005-5.0 |
| PEG-40 hydrogenated castor oil | 0.50-2.00 |
| Parfum | 0.10-0.30 |
| Hydroxypropyl guar | 0.10-0.40 |
| Ethoxydiglycol | 0.10-0.70 |
| Lactic acid | 0.05-0.50 |
| Aqua | qs to 100 mL |

The following is the description of an experimental study of the action of a compound based on this invention during its use.

Activity Study

Tissue Samples

The skin of the normal human scalp was taken from a woman who was submitted to routine facial lifting surgery, after obtaining her informed consent. All experiments were performed in compliance with the Helsinki principles, with the Ethics Committee approval.

Microdissection of Hair Follicles and Organ Culture

Hair follicles (HF) in anagen phase VI with normal pigmentation (the study did not include grey/white hair follicles) were microdissected from normal human scalp skin and subjected to organ culture based on Philpott's model.

$N^1$-methyl-spermidine in the invention or the carrier as such (control group) were administered once every time the culture medium was changed, namely every 48 hours. The control compound administered was spermidine at a concentration of 0.5 μM.

Hair Pigmentation

The Masson-Fontana stain was administered to ensure histochemical visibility of melanin in frozen sections. Melanin was stained as brown granules and the degree of pigmentation was assessed with the quantitative Masson-Fontana technique. (Ito N., Ito T., Kromminga A., Bettermann A., Takigawa M., Kees F., Straub R. H., and Paus R. (2005): Human hair follicles display a functional equivalent of the hypothalamic-pituitary-adrenal axis and synthesise cortisol. (*FASEB J* 19, 1332-4)

This method is a highly sensitive and reliable indicator of variations in melanin synthesis, as proven by assays of enzymatic activity, and the expression of standard tyrosinase. (Kauser S., Slominski A., Wei E. T., and Tobin D. J. (2006): Modulation of the human hair follicle pigmentary unit by corticotropin-releasing hormone and urocortin peptides. (*FASEB J* 20, 882-95)

The intensity of the stain was analysed in a defined reference region of the hair follicle's pigmentation unit using the software ImageJ (National Institute of Health).

RESULTS

Figure 1:
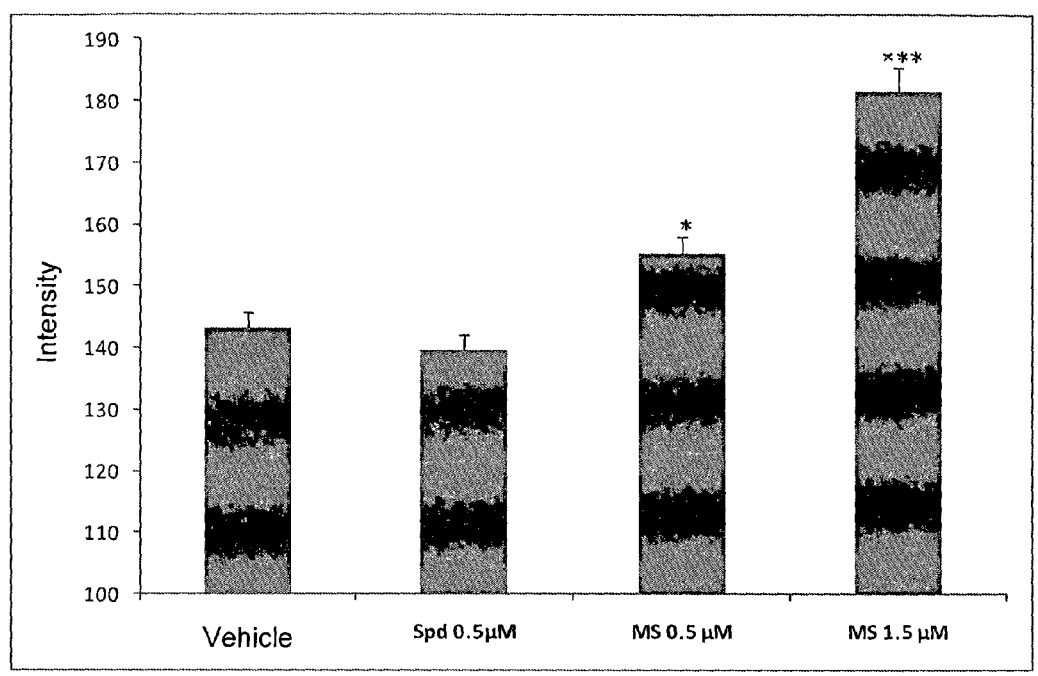
FIGS. 1 and 2 of the enclosed drawings show the results of an experimental study.
Figure 2:
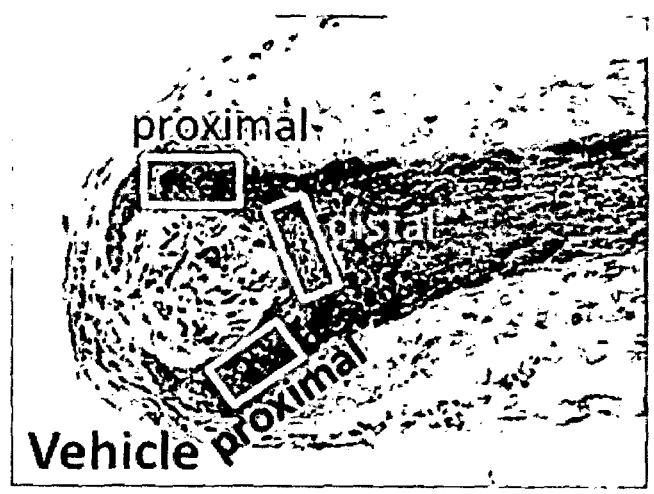
Figure 2:
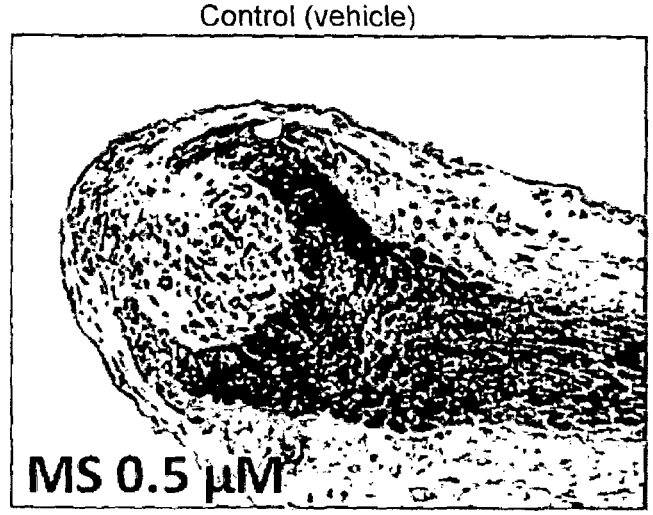
Figure 2:
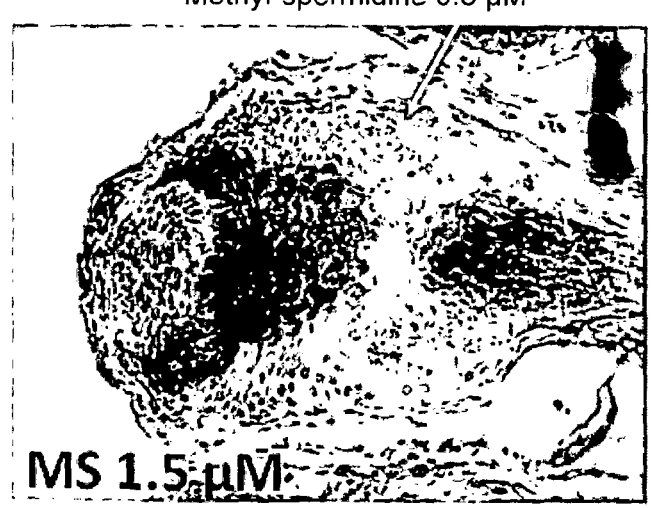

FIGS. 1 and 2 of the enclosed drawings show the results of the above-described experimental study.

$N^1$-methyl-spermidine is identified herein with the initials MS. The initials Spd identify spermidine used as a control compound.

FIG. 1 shows a graph of the (absolute) intensity of pigmentation in hair follicles measured and compared between the control group treated only with the carrier, the groups treated with $N^1$-methyl-spermidine (MS) in a concentration of 0.5 and 1.5 µM, respectively, and, lastly, the reference group treated with spermidine (Spd) in a concentration of 0.5 µM.

FIG. 2 shows the corresponding images based on the histochemical study of melanin with the Masson-Fontana stain for the control group treated only with the carrier, and for the groups treated with $N^1$-methyl-spermidine (MS) in a concentration of 0.5 and 1.5 µM, respectively.

The image of the carrier distinguishes the proximal and distal areas of the pigmented region, as indicated.

Both FIGS. 1 and 2 highlight the increase in melanin produced in case of treatment with $N^1$-methyl-spermidine at both concentrations tested in a dose-dependent manner; hence, the considerable melanogenetic activity in hair treated with this compound, compared to the reference carrier.

The graph in FIG. 1 also shows the higher increase in absolute pigmentation intensity in hair follicles when $N^1$-methyl-spermidine (MS) is used in a concentration of 0.5 µM, compared to the reference group treated with spermidine (Spd) in the same concentration, 0.5 µM.

Enzymatic Assay of Tyrosinase

Figure 3:
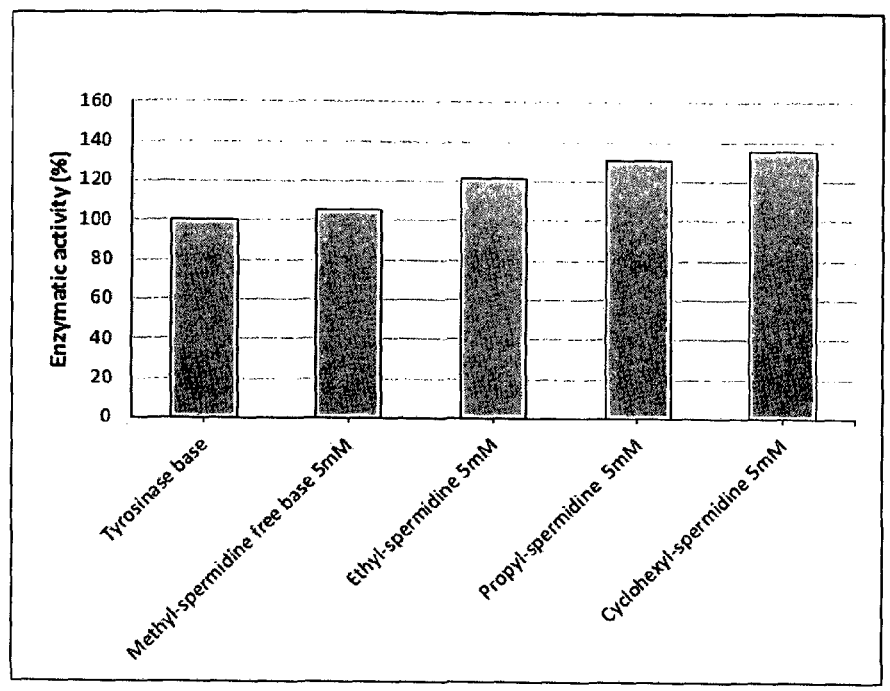
FIGS. 3 and 4 of the enclosed drawings show the results of another experimental study.
Figure 4:
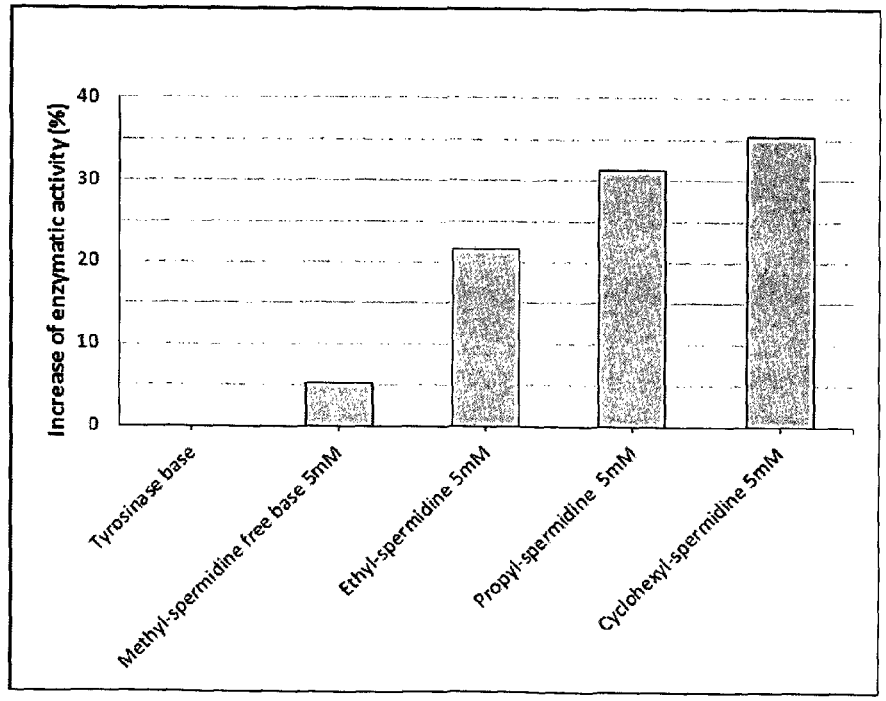

FIGS. 3 and 4 of the enclosed drawings show the results of the additional experimental study described below.

The following compounds with formulae (II), (III), (IV) and (V) were tested as defined above, all in a concentration of 5 mM:

| | |
|---|---|
| Methyl-spermidine (base) | Formula (II) |
| Ethyl-spermidine | Formula (IV) |
| Propyl-spermidine | Formula (V) |
| Cyclohexyl-spermidine | Formula (III) |

Principle of the Assay

Tyrosinase is a membrane glycoprotein that is expressed in melanosomes, specialised organelles in the endocytic pathway through which the synthesis and assembly of melanin takes place. The synthesis of melanin from tyrosine takes place in pigment-producing cells, namely melanocytes. Melanin produced in melanosomes is transferred to keratinocytes through said processes. Melanin is a polymer that absorbs light within a broad spectrum of wavelengths, and protects keratinocytes from the harmful effects of UV radiations. A peroxidase is involved in the first phase of the reaction, which converts the amino acid into 2,3-dihydroxyphenyl alanine or DOPA. The enzyme tyrosinase is involved in the subsequent phase of the biosynthesis pathway that produces dopaquinone. Melanin is synthesised starting from precursors of tyrosine and DOPA, through the enzyme tyrosinase, which presents both hydrolase and oxidase functions. Tyrosine is converted into L-DOPA (dihydroxyphenylalanine) and, then, into dopaquinone, which is red, until the brown melanin polymer is obtained. In a first branch of the pathway dopaquinone is converted into black polymeric melanins, while the reaction with cysteine forms a series of polymers that are similar among them and are called red polymeric melanins.

Materials

Monobasic potassium phosphate (Sigma P5379-100G)
   L-tyrosine (Sigma T3754-50G)
   Tyrosinase (Sigma T3824-25KU)
   Potassium hydroxide, standard solution (Sigma 35113-1L)
   Water (BioChemika, for molecular biology, DEPC-treated and sterile filtered) (Sigma, 95284)

Instruments

Cuvettes 100-QS (Helima, Z600105)
   Sterile nozzle tips with filter
   Spectrophotometer (Jenway UVNIS MOD:6715, BS-6715B0)
   pH-meter 827 pH Lab (Metrhom)

Procedure

REAGENT A (potassium phosphate buffer, 50 mM, pH 6.5, 25° C.):
   Correct the pH (approx. 4.5) to pH 6.5 with KOH 1M;
   Store at 4° C. until use.
   REGENT B (L-tyrosine solution 1 mM):
   Store at 4° C. until use.
   REAGENT C (tyrosinase solution):
   Just before use:
   The enzyme has a volume of xxxx units/mg solid (indicated on the bottle and, therefore, it differs every time a different bottle is used).
   Calculate the corresponding liquid=xxxx units/mL liquid.
   =xxxx units/mL liquid/xxxx units/mg solid=x mg/mL
   Prepare portions of about 1 mL and preserve in aluminium paper at −20° C. until use.
   Prepare a solution A+B as described below:
   9 mL of deionised water
   10 mL of Reagent A (potassium phosphate buffer 50 mM)
   10 mL of Reagent B (L-tyrosine 1 mM)
   Vortex the solution and, if necessary, restore pH 6.5, at 25° C. with HCl 1M or NaOH.

Prepare the solutions with the various concentrations of the compounds to be tested, and preserve at 4° C. until use.

Defrost the tyrosinase solution and keep it on ice in the dark until use.

Mix, at ambient temperature, the solution of potassium phosphate buffer (50 mM, pH 6.5), the above solution A+B and the solutions that include the compounds of the formula (I) to be tested.

Start up the spectrophotometer for calibration.
Use the following parameters:
Reading: 280 nm;
Measuring mode: absorbance;
Execution settings: 700 seconds.
The rest is as per the default procedure.

First read the enzymatic activity of tyrosinase when there is only L-tyrosine to verify the actual enzyme/mL units and have a basic reference to later assess the effects of the compound examined on enzyme activity:

1 replicates for the blank test (one blank test for each concentration to be tested);

2 replicates for the test (one test for each concentration to be tested).

Perform a reading of the blank test of the instrument (no cuvette)→Cal.

Prepare the mixtures in separate cuvettes, as described below:

| Order | TEST TUBE | Blank Test | Test |
|---|---|---|---|
| 1 | Solution A + B | 2.90 mL | 2.90 mL |
| 2 | Reagent A (buffer) | 0.1 mL | / |
| 2 | Reagent C (Tyrosinase solution) kept on ice | / | 0.1 mL |

Test the examined compounds with formulae (II), (III), (IV) and (V), as specified below:

1 replicates for the blank test (one blank test for each concentration to be tested);

2 replicates for the test (one test for each concentration to be tested).

Prepare the mixtures in separate cuvettes, as described below:

| Order | TEST TUBE | Blank Test | Test |
|---|---|---|---|
| 1 | Solution A + B | 2.90 mL | 2.80 mL |
|   | Reagent A (buffer) | / | / |
| 3 | Reagent C (Tyrosinase solution) kept on ice | / | 0.1 mL |
| 2 | Compound with formula (I) to be tested | 0.1 mL | 0.1 mL |

Calculating the Inhibition or Induction of Enzymatic Activity

Units/mL of enzyme =

$$\frac{(\Delta A_{280nm}/\text{min Test} - \Delta A_{280nm}/\text{min Blank Test})\,(df)}{(0.001)(0.1)}$$

df=dilution factor (30 because 0.1 mL/3 mL tot)

0.001=change of $A_{280\ nm}$/min per unit of L-tyrosine at pH 6.5, 25° C. in a 3 mL reaction mixture;
0.1=volume (mL) of enzyme used
Unit/mg solid=unit/mL of enzyme: mg solid/mL of enzyme
Unit/mg protein=unit/mL of enzyme: mg protein/mL of enzyme
Definition of unit=increment of $A_{280\ nm}$/min equal to 0.001, at 25° C., pH 6.5 in a 3 mL reaction volume containing L-tyrosine.

The percentage of enzymatic activity was calculated for each tested compound, compared to the activity of the enzyme (100% enzymatic activity) failing the presence of active compounds.

The increment percentage of enzymatic activity was later calculated (% enzymatic activity−100).

| Results | Enzymatic activity (%) | Increment in enzymatic activity (%) |
|---|---|---|
| Tyrosinase base | 100.00 | |
| Methyl-spermidine 5 mM | 105.16 | 5.16 |
| Ethyl-spermidine 5 mM | 121.50 | 21.50 |
| Propyl-spermidine 5 mM | 131.29 | 31.29 |
| Cyclohexyl-spermidine 5 mM | 135.31 | 35.31 |

Data reported in the above tables are summarised in the graphs in FIGS. 3 and 4.

FIG. 3 shows the absolute data of enzymatic activity (%).
FIG. 4 shows the respective increments in enzymatic activity (%) thus measured, compared to the control.

All tested compounds of formula (I) show an evident increase in the enzymatic activity of tyrosinase and, therefore, in the melanogenetic activity concerned by the invention.

The invention claimed is:

1. Composition useful in promoting pigmentation of hair comprising at least one compound selected from the group consisting of:

$N^1$-methyl spermidine of formula $H_2N$—$(CH_2)_3$—$N^1(CH_2)_4$—$NH_2$ $N^1$-cyclohexyl-spermidine of formula $H_2N$—$(CH_2)_3$—$N^1(C_6H_{11})$—$(CH_2)_4$—$NH_2$ $N^1$-ethyl-spermidine of formula $H_2N$—$(CH_2)_3$—$N^1(C_2H_5)$—$(CH_2)_4$—$NH_2$ and $N^1$-propyl-spermidine of formula $H_2N$—$(CH_2)_3$—$N^1(C_3H_7)$—$(CH_2)_4$—$NH_2$ formulated as active ingredient with excipients for topical administration to the scalp.

2. The composition of claim 1, wherein said compound is $N^1$-methyl spermidine of formula:

$$H_2N\text{—}(CH_2)_3\text{—}N^1(C_6H_{11})\text{—}(CH_2)_4\text{—}NH_2 \quad (II).$$

3. The composition of claim 1, wherein said compound is $N^1$-cyclohexyl spermidine of formula:

$$H_2N\text{—}(CH_2)_3\text{—}N^1(C_6H_{11})\text{—}(CH_2)_4\text{—}NH_2 \quad (III).$$

4. The composition of claim 1, wherein said compound is $N^1$-ethyl-spermidine of formula:

$$H_2N\text{—}(CH_2)_3\text{—}N^1(C_2H_5)\text{—}(CH_2)_4\text{—}NH_2 \quad (IV).$$

5. The composition of claim 1, wherein said compound is $N^1$-propyl-spermidine of formula:

$$H_2N\text{—}(CH_2)_3\text{—}N^1(C_3H_7)\text{—}(CH_2)_4\text{—}NH_2 \quad (V).$$

* * * * *